US012582760B1

(12) United States Patent
　　Gutierrez

(10) Patent No.: US 12,582,760 B1
(45) Date of Patent: Mar. 24, 2026

(54) CLOG REMOVING DEVICE FOR MEDICAL TUBING

(71) Applicant: Frank Gutierrez, Naples, FL (US)

(72) Inventor: Frank Gutierrez, Naples, FL (US)

( * ) Notice: Subject to any disclaimer, the term of this patent is extended or adjusted under 35 U.S.C. 154(b) by 962 days.

(21) Appl. No.: 17/832,888

(22) Filed: Jun. 6, 2022

(51) Int. Cl.
　　*A61M 1/00* 　　　(2006.01)
　　*B08B 9/027* 　　　(2006.01)
　　*A61M 25/00* 　　　(2006.01)

(52) U.S. Cl.
　　CPC .............. *A61M 1/83* (2021.05); *B08B 9/027* (2013.01); *A61M 2025/0019* (2013.01); *A61M 2209/10* (2013.01); *B08B 2209/027* (2013.01)

(58) Field of Classification Search
　　CPC . A61M 1/83; A61M 2025/0019; B08B 9/027; B08B 2209/027; B08B 2209/04
　　See application file for complete search history.

(56) References Cited

U.S. PATENT DOCUMENTS

| | | | | |
|---|---|---|---|---|
| 4,452,244 A | * | 6/1984 | Chin | ...................... A61M 1/83 |
| | | | | 606/209 |
| 4,825,676 A | * | 5/1989 | Diggins | .............. B21D 19/043 |
| | | | | 72/409.18 |
| 10,471,189 B2 | | 11/2019 | O'keefe et al. | |
| 10,974,023 B2 | | 4/2021 | O'keefe et al. | |

* cited by examiner

*Primary Examiner* — Deanna K Hall
(74) *Attorney, Agent, or Firm* — Sanchelima & Associates, P.A.; Christian Sanchelima; Jesus Sanchelima

(57) ABSTRACT

A clog removing device for medical tubing including a hand tool which is composed by handle members which have an electric system attached to one of the handle members. The hand tool has a gripping portion placed on one distal end of the handle members to grab the hand tool. The electric system is connected to a bottom which is placed on a top surface of the gripping portion to activate a couple of motors concentrically attached to cylindrical roller members. The hand tool is formed by the handle members which are interlocked by a fastening member which has a spring configuration to allow the hand tool open through the roller members by compressing the distal ends of the handle. The hand tool is configured to have inserted a medical tubing among the roller members and remove any inner substance thereof.

5 Claims, 3 Drawing Sheets

CLOG REMOVING DEVICE FOR MEDICAL TUBING

BACKGROUND OF THE INVENTION

1. Field of the Invention

The present invention relates to a clog removing device for medical tubing and, more particularly, to a clog removing device for medical tubing that removes obstructions in medical tubing by squeezing a segment of a medical tubing by a pair of compressive rollers which move the obstructions from the tubing to the exit thereof.

2. Description of the Related Art

Several designs for a blog removing device for medical tubing have been designed in the past. None of them, however, include a pair of compressive rollers mounted on a handheld tool which allows to remove any obstruction from the segment of medical tubing.

Applicant believes that a related reference corresponds to U.S. Pat. No. 10,471,189 issued for a device for cleaning obstructions in medical tubing. Applicant believes that another related reference corresponds to U.S. Pat. No. 10,974,023 issued for a device for clearing obstructions in medical tubing. None of these references, however, teach of an electric hand tool for removing obstructions in medical tubing that is comprised of a handheld tool with a pair of compressive rollers which are used to squeeze a segment of medical tubing and then move down the tubing towards the exit of the tubing, forcing out any obstructions.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a pair if compressive rollers on a handheld tool.

It is another object of this invention to provide a motorized system for the compressive rollers.

It is still another object of the present invention to provide a removing device for segments of medical tubing.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
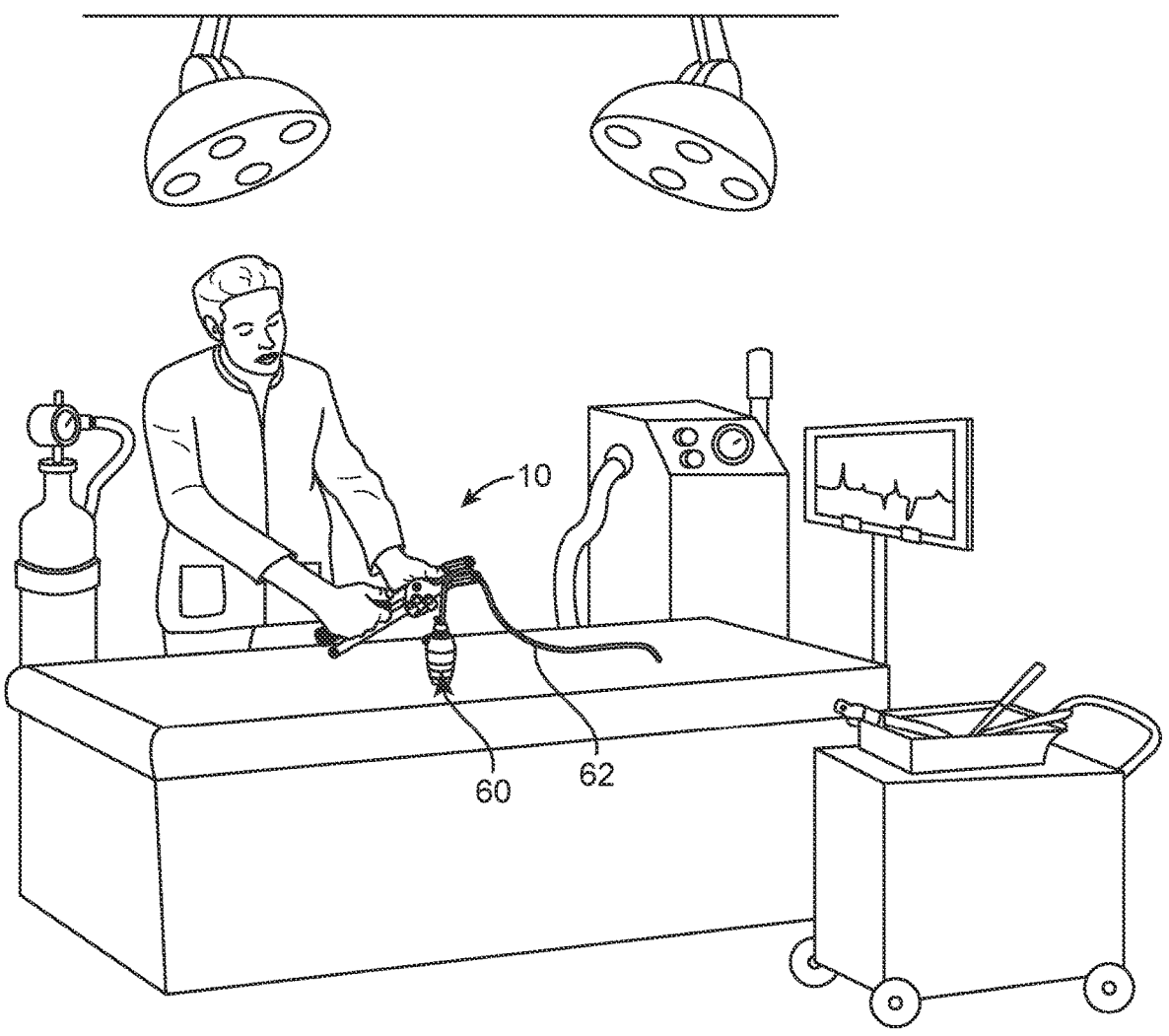
FIG. 1 represents an operational view of the present invention 10.

Referring now to the drawings, where the present invention is generally referred to with numeral 10, it can be observed that it basically includes a hand tool assembly 20, an electric system assembly 40 and a tube assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The hand tool assembly 20 includes a hand tool 22, handle members 23, ripping portions 24, roller members 25, a fastening member 26, and a spring 27. The hand tool 22 has an elongated scissor body as best observed in FIG. 2 which is formed by the handle members 23. The hand tool 22 and the handle members 23 may be made of aluminum material. Nevertheless, in other embodiments, the hand tool 22 and the handle members 23 may be made of a metal material, steel material, rigid plastic material, wood material, plastic material, or any other variation thereof. It is to be understood that the hand tool 22 may be interlocked by the fastening member 26 which is configured as a spring that hold the hand tool 22 opened. In a suitable embodiment, hand tool 22 may be configured to be closed by each of the handle members 23 when applying force thereof. Handle members 23 may have a tubular body wherein one of the handle members 23 has a tubular body with a curved central portion which allows to interlock both handle members 23 by the fastening member 26. Both handle members 23 have a curved portion which extend from each of the distal ends. In one embodiment, one of the handle members 23 has a gripping portion 24 which is placed to a distal end thereof. It is to be considered that at least two of the distal ends of the handle members 23 may be positioned close to each other wherein the roller members 25 may be placed.

Figure 2:
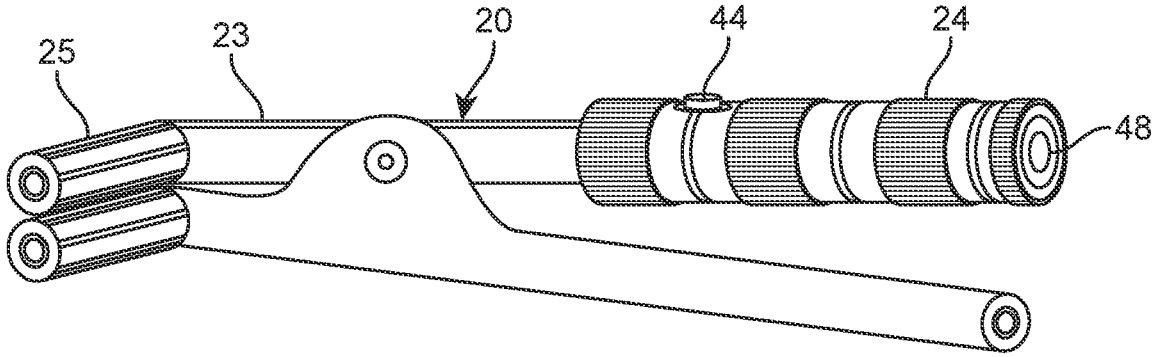
FIG. 2 shows an isometrical view of the hand tool assembly 20 wherein is shown the handle members 23 and the roller members 25.

As best shown in FIG. 2 gripping portion 24 may have a cylindrical body which conforms with the body of the distal end of one of the handle members 23. In a suitable embodiment, the gripping portion 24 may be configured to hold the hand tool 22 and store a button on the side thereof. The gripping portion 24 may be configured to allow grab the hand tool 22. In a suitable embodiment, the gripping portion 24 may be made of a rubber material. Nevertheless, in other embodiments, the gripping portion 24 may be made of a plastic material, polymer material, or any other variation thereof. In a suitable embodiment, the handle members 23 may have the roller members 25 wherein each of the roller members 25 is attached to the distal of the handle members 23 considering the curved portion that extends thereof. Roller members 25 may have a cylindrical body which conforms with the curved distal portion that extends from each of the handle members 23. In a suitable embodiment, the roller members 25 may be made of a rubber material. Nevertheless, in other embodiments the roller members 25 may be made of a plastic material, metal material, wood material, steel material, or any other variation thereof. In a preferred embodiment, roller members 25 may be configured to be operated and spined by the electric system assembly 40. It is to be understood that each of the roller members 25 may be adjacent to each other by the contour of each of the roller members 25 as best observed in FIG. 2.

Figure 3:
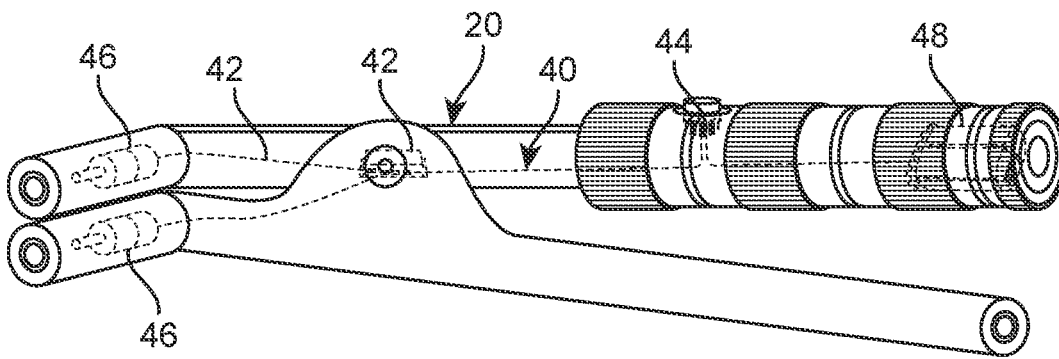
FIG. 3 illustrates an internal view of the hand tool assembly 20 wherein an electrical system assembly 40 is shown.
Figure 4:
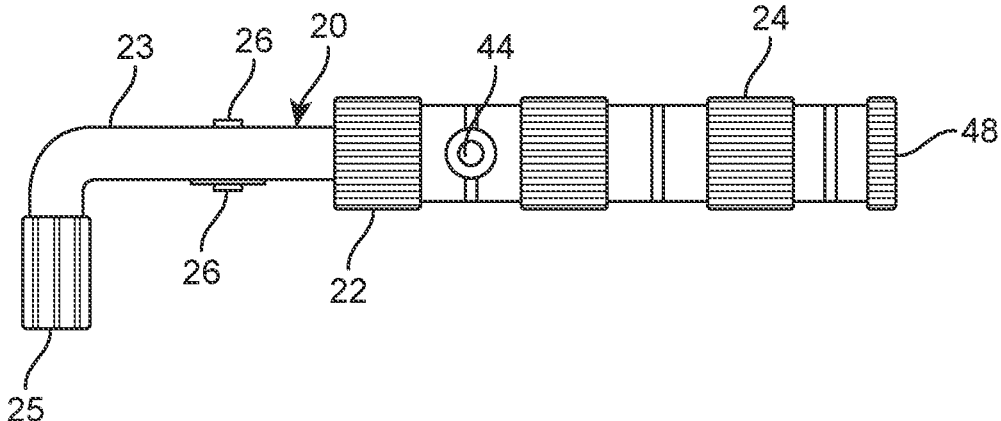
FIG. 4 is a representation of a side view of the hand tool 22.

As best observed in FIG. 4 the fastening member 26 may be attached to a central portion of the handle members 23. In a suitable embodiment, the fastening member 26 may have a cylindrical body as shown in FIG. 3. Nevertheless, other bodies like square prism, rectangular prism, octagonal prism, hexagonal prism, or any other variation thereof may be suitable for the fastening member 26. In a preferred embodiment, the fastening member 26 may be configured with a spring to allow the hand tool 22 open the distal ends wherein the roller members 25 are attached to allow insert the tube assembly 60.

The electric system assembly 40 includes an electric system 42, a button 44, motors 46, and a battery 48. The electric system 42 may have a rectangular body with wires on the sides. Nevertheless, other bodies like square, cylindrical, or any other variation thereof, may be suitable for the electric system 42. In one embodiment, electric system 42 may be made of a plastic material with copper material. In other embodiment, electric system 42 may be attached in the inner of at least one of the handle members 23. Electric system 42 may allow hand tool 22 operate by the roller members 25 which are propelled by the motors 46. It is to be considered that electric system 42 may be relate to the button 44, the motors 46 and the battery 48. The button 44 may be attached to the inner of the gripping portion 24 as best illustrated in FIG. 3. In a suitable embodiment, the button 44 may have a cylindrical body with a square bottom body. The button 44 may allow engine the motors 46 which propel the roller members 25. In one embodiment button 44 may be made of a plastic material. Nevertheless, in other embodiments, button 44 may be made of a polymer material, ceramic material, rubber material, or any other variation thereof.

As best shown in FIG. 3 the motors 46 may have a shape that conforms with the shape of the roller members 25. It is to be considered that motors 46 may be attached to the distal ends of the handle members 23 wherein the rollers members 25 are placed on. It is to be considered that motors 46 may be made of a metal body including copper wires therein. In one embodiment, motors 46 may be a type of AC brushless motors. Nevertheless, in other embodiments, motors 46 may be a type of DC brushed motors, direct drive motors, linear motors, servo motors, stepper motors, or any other variation thereof. Each of the motors 46 may be concentrically placed with each of the roller members 25 as best observed in FIG. 3. In a suitable embodiment, the battery 48 may be made of a lithium material. The battery 48 may be suitable to have a body that conforms with the body of the gripping portion 24 which may be a cylindrical body. In one embodiment, battery 48 may be a rechargeable battery which may need battery cells. In another embodiment, the battery 48 may be a removable battery 48 which can be extracted from the distal end of one of the handle members 23 and be charged with external options. It is to be understood that battery 48 may be configured to provide power supply to the electric system 42 allowing to operate the hand tool 22 and remove any substance from the inner of the tube assembly 60.

The tube assembly 60 includes a tube 62. The tube 62 may be a medical tubing. In a suitable embodiment tube 62 may be inserted to among the roller members 25 for then start the electric system 42 by the button 44 which activates the motors 46 and make spin the roller members 25.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A clog removing device for medical tubing, comprising:

a hand tool assembly including a hand tool wherein a pair of handle members are interlocked by a central portion to form the hand tool; wherein said central portion receives a fastener to create a pivot that holds the pair of handle members together and allows pair of handle members to rotate around that central portion; wherein each of said pair of handle members has an L-shape, wherein a vertical component of each handle member is longer than the horizontal component; wherein said handle members comprise a first handle member and a second handle member; wherein said first handle member has a griping portion covering a portion of a length thereof below said central portion; wherein each handle member includes a roller member located at a proximal end of the horizontal component;

an electric system assembly including a button, motors and a battery; wherein said battery is inserted into a bottom end of the first handle member; wherein said button is located on said gripping portion; wherein the motors are coupled to each proximal end of each handle member and said motors are attached to said roller member; wherein the button actuates the motors to rotate the roller members; and wherein a tube is placed between the roller members, when the roller members are actuated by said button, the roller members squeeze said tube, thereby forcing out obstructions inside said tube.

2. The clog removing device for medical tubing of claim 1, wherein said roller members have a hollow cylindrical body.

3. The clog removing device for medical tubing of claim 1, wherein said electric system is connected to said button and motors, wherein the motors are powered by a battery.

4. The clog removing device for medical tubing of claim 1, wherein each one of the motors is concentrically attached inside of each of the roller members.

5. A clog removing device for medical tubing, consisting of:

a hand tool formed by a pair of handle members which are interlocked at a central portion; wherein said central portion receives a fastener to create a pivot that holds the pair of handle members together and allows pair of handle members to rotate around that central portion; wherein each of said pair of handle members has an L-shape, wherein a vertical component of each handle member is longer than the horizontal component; wherein said handle members comprise a first handle member and a second handle member; wherein said first handle member has a griping portion covering a portion of a length thereof below said central portion; wherein said second handle member has a curved protrusion to denote the central portion of the hand tool where the fastener is inserted; wherein each handle member includes a roller member located at a proximal end of the horizontal component; wherein each roller member has a cylindrical shape; each roller member is made of rubber;

an electric system assembly including a button, motors and a battery; wherein said battery is inserted into a bottom end of the first handle member; wherein said button is located on said gripping portion; wherein the motors are coupled to each proximal end of each handle member and said motors are attached to said roller member; wherein the button actuates the motors to rotate the roller members; wherein the electric system assembly is electrically wired inside the hand tool; and wherein a tube is placed between the roller members, when the roller members are actuated by said button, the roller members squeeze said tube, thereby forcing out obstructions inside said tube.

* * * * *